United States Patent [19]
D'Angelo et al.

[11] Patent Number: 6,024,975
[45] Date of Patent: Feb. 15, 2000

[54] METHOD OF TRANSDERMALLY ADMINISTERING HIGH MOLECULAR WEIGHT DRUGS WITH A POLYMER SKIN ENHANCER

[75] Inventors: Joseph P. D'Angelo, Miami; Henry Schur, Hallandale, both of Fla.

[73] Assignee: Americare International Diagnostics, Inc.

[21] Appl. No.: 08/745,496

[22] Filed: Nov. 12, 1996

Related U.S. Application Data

[63] Continuation-in-part of application No. 08/588,003, Jan. 17, 1996, abandoned, which is a continuation of application No. 08/141,199, Oct. 21, 1993, abandoned, which is a continuation-in-part of application No. 07/865,309, Apr. 8, 1992, abandoned.

[51] Int. Cl.[7] .................................................. A61F 13/00
[52] U.S. Cl. ......................... 424/449; 514/944; 514/946; 424/70.15; 424/448
[58] Field of Search .................................... 424/448, 449, 424/70.15; 514/944, 946

[56] References Cited

U.S. PATENT DOCUMENTS

| | | | |
|---|---|---|---|
| 4,573,996 | 3/1986 | Kwiatek et al. | 424/434 |
| 4,624,665 | 11/1986 | Nuwayser | 604/307 |
| 4,666,441 | 5/1987 | Andriola et al. | 424/448 |
| 4,952,560 | 8/1990 | Kigasawa | 514/2 |
| 5,162,043 | 11/1992 | Lew | 604/20 |
| 5,225,192 | 7/1993 | Lovrecich | 424/78.01 |
| 5,232,703 | 8/1993 | Blank | 424/449 |
| 5,234,957 | 8/1993 | Mantelle | 424/485 |
| 5,252,334 | 10/1993 | Chiang et al. | 424/448 |

OTHER PUBLICATIONS

"Controlled–Release Technology" Lee et al., 1986.

*Primary Examiner*—D. Gabrielle Brouillette
*Attorney, Agent, or Firm*—Herbert L. Lerner; Laurence A. Greenberg

[57] ABSTRACT

A high molecular weight drug is transdermally administered by applying a polymer skin enhancer and a drug active to the skin of the patient. The drug active has a molecular weight of above 50 daltons and takes at least 15% by weight of the system. The drug may be encapsulated or the drug solution may be partly encapsulated and partly free. The skin enhancer is polyvinylpyrrolidone (PVP) and it is mixed at between 7 and 35% of the drug. A gelling agent may be optionally added at up to 20% by volume. The chemical system is preferably administered via a multidose transdermal drug patch assembly which includes a drug-impervious support impressed to form a series of compartments. Each compartment is a reservoir for a unit dose of a drug active to be transdermally administered. The support is adhesively secured to the skin of a patient. Individual devices are provided for resealably enclosing the drug active in each of the reservoirs. The individual enclosing devices are removable to release the unit dose into contact with the skin of the patient and are actuable to control the transdermal absorption of the drug actives. The drug may also be administered in a creme.

24 Claims, 10 Drawing Sheets

METHOD OF TRANSDERMALLY ADMINISTERING HIGH MOLECULAR WEIGHT DRUGS WITH A POLYMER SKIN ENHANCER

CROSS-REFERENCE TO RELATED APPLICATIONS

This is a continuation-in-part of copending application Ser. No. 08/588,003, filed Jan. 17, 1996 now abandoned which was a continuation of application Ser. No. 08/141,199, filed Oct. 21, 1993, now abandoned; which was a continuation-in-part of application Ser. No. 07/865,309, filed Apr. 8, 1992, now abandoned.

BACKGROUND OF THE INVENTION

1. Field of the Invention

The invention relates to the transdermal delivery of drugs, particularly in connection with patch systems which allow for the variable dosage and/or multiple dosage of medicament in a patient controllable or pre-set format.

2. Description of the Related Art

Transdermal drug administration has recently come to the forefront as a useful route for continuous dosing of useful drugs where other means of administration are either discontinuous, labor intensive or where other routes present absorption or inactivation problems. Skin drugs which are administered through the skin are not subject to liver metabolism. Per os administration has been time honored i.e. "a teaspoonful three times a day". Such unit dose administration, however, is subject to the first pass liver metabolism, non-uniform absorption from the gut due to other gut contents or inactivation of the drug actives by the digestion process. This leads to erratic blood levels of the actives. In addition, the need for active periodic administration i.e. three times a day, required active and willing participation by the patient or in home or hospital settings by the caregiver. Due to the afore-mentioned disadvantages and, last but not least, due to its non-invasive character, transdermal administration has recently become very popular.

The shortcomings of invasive and metabolised drug administration are obviated by transdermal application where possible, of the drugs. A patch is adhered to a clear area of the skin and the drug is continually absorbed through the skin into the bloodstream for systemic distribution.

Selectable and variable dosage transdermal administration has been proposed in several of our copending applications. For instance, the parent of this application, entitled "A Multidose Transdermal Patch Assembly" pertains to trans-dermal medication assemblies and more particularly to such assemblies consisting of multiple unit-dose reservoirs with each reservoir having individual tear and release resealable closure means for initiation and administration of the medication. The transdermal delivery of high molecular weight drugs, as for instance insulin or calcitonin, is disclosed therein.

The upper layer of the epidermis (stratum corneum) was previously considered an impenetrable barrier in terms of drug delivery. The advent of skin enhancers has vastly improved the administration of low molecular weight drugs.

It has not been possible heretofore, however, to administer heavy molecules such as, for instance, insulin and calcitonin, i.e. not to any therapeutical level. A skin enhancement system and system adsorption theory are explained in more detail in the enclosed FIG. 14, in conjunction with the corresponding description.

The skin is particularly useful as it presents large areas for drug administration, as the skin is the largest organ of the body. The utility of such a mode of administration has been promoted with the discovery and development of a group of compounds that promote transdermal penetration of the various active drugs. Such compounds are known in the art as penetration enhancers or skin enhancers. They are generally characterized to be from the group of monovalent branched or unbranched aliphatic, cycloaliphatic or aromatic alcohols of 4–12 carbon atoms; cycloaliphatic or aromatic aldehydes or ketones of 4–10 carbon atoms, cycloalkanoyl amides of C 10–20 carbons, aliphatic, cycloaliphatic and aromatic esters, N,N-di-lower alkylsulfoxides, unsaturated oils, terpenes and glycol silicates.

These compounds and their specific activity as penetration enhancers, are more fully discussed in the text "Transdermal Delivery of Drugs, A. F. Kydonieus (ED) 1987 CRL Press and in such U.S. Patents as U.S. Pat. Nos. 4,913,905, 4,917,676 and 5,032,403.

As a result of these penetration enhancers, almost any drug, to some degree, can be administrated transdermally cf. U.S. Pat. Nos. 4,917,676, 3,598,122; 3,598,123; 3,742,951; 3,797,494; 3,948,254; 3,996,734; 4,284,444; and 4,597,961. Examples of such pharmacological actives include administra-tion of antibacterial such as the penicillins, tetracyclines, second and third generation cephalosporins, chloramphenicol sulfonamides; sedatives and/or hypnotics, such as barbitu-rates, carbromal, antitussives such as codeine and dextro-methorphan; anti-anxiety drugs such as the benzodiazepines including diazepam, buspirone; psychostimulants such as imipramine, amitriptyline and other tricyclic antidepressants; anti psychotic drugs and tranquilizers such as lithium, chlorpromazine and haloperidol, reserpine, thiopropazate; Parkinsonism control agents such as bromotriptine, percolide, the anticholinergics including benzotropine, procyclidine, amantadine (also an antiviral); hormones and hormone antagonists and agonists, including adrenocorticosteroids; insulin, androgenic steroids, estrogenic and pro-gestrogenic steroids, thyroxin and its agonist 5-FU(fluorouracil), tamoxifen; antipyretics and analgesics such as aspirin/acetaminophen and other non-steroidal anti-inflammatory drugs (NSAID), analgesics based on morphine; morphine antagonists; vasodilating agents such as nitroglycerine, isorbide dinitrate; alpha and beta-blockers and other cardioactive drugs; antimalarials; antihistamines and anticholinergics including atropine, hyoscyamine or methscopalomine (for motion sickness); weaning agents such as nicotine (for tobacco addiction); and antiasthmatic bronchodilators such as formoterol; and combinations of such pharmaceutical actives.

Of course, while feasible, not all of these actives have yet been completely tested for efficacy by transdermal administration but many are under vigorous scrutiny. Other actives at this time are not economically viable for such administration, as the cost of full safety testing is too great for the specific number of patients involved. The last paragraph of this specification, lists a number of promising drugs which are currently under intense scrutiny by us.

It is noted, in particular, that high molecular weight drugs have not yet been reported in the art as candidates for successful transdermal penetration. Emphasis is placed, in the context of this disclosure, on insulin and calcitonin. The latter hormone is a dotriacontapeptide which was first discovered in 1962. Calcintonins, originally found in and isolated from the thyroid gland of the hog, have meanwhile been synthesized in various forms. Generally, seven genuine hormones are listed under the names Hog, Man, Beef, Salmon, Sheep, Chicken, Eel and Rat, in accordance with their origin. The therapeutic use of calcitonins (particularly synthesized calcitonins) is widely reported. Due to their high molecular weight (in the vicinity of 6000 daltons), it has not been possible to transdermally administer the same.

SUMMARY OF THE INVENTION

It is an object of this invention to provide a viable system and method for the transdermal administration of high molecular weight drugs of upward of 50 daltons with a polymer skin enhancer. It is a particular object to provide the system and the method in the context of multiple unit-dose transdermal patch assemblies and an electronic delivery system.

With the foregoing objects of the invention in view there is provided, in accordance with the invention, a polymer system for effecting delivery of high molecular weight drug actives by transdermal administration. The system includes at least 15% by weight of a drug active having a molecular weight of more than 50 daltons, a polymer which is polyvinylpyrrolidone, a weight of the polymer being 7 to 35% by weight of the drug active, and an optional gelling agent having from 0 to 20% by volume of the system.

The drug active is preferably Calcitonin.

There is also provided a method of transdermally administering a high molecular weight drug, which comprises: applying to skin of a patient a polymer skin enhancer, and applying to the skin of the patient a drug active (15% or more of the system) having a molecular weight of above 50 daltons and preferably above 500 daltons. The preferred polymer skin enhancer is polyvinylpyrrolidone.

The method further comprises mixing the drug active and the polymer skin enhancer in a ratio such that the polymer skin enhancer is 7 to 35% by weight of the drug active, and subsequently simultaneously applying the polymer skin enhancer and the drug active to the skin of the patient. It is also possible to add a gelling agent of up to 20% of total volume to the polymer skin enhancer and the drug active prior to applying to the skin of the patient.

With the foregoing and other objects in view there is also provided, in accordance with the invention, a polymer system for promoting delivery of high molecular weight drug actives by transdermal administration, comprising: a drug active having a molecular weight of more than 50 daltons and a drug weight, a polymer, a weight of said polymer being 7 to 35% by weight of the drug weight of said drug active, and an optional gelling agent having from 0 to 20% by volume of the system.

The drug active of the polymer system may be a hormone, i.e. calcitonin. The polymer may be a biocompatible polymer of the pyrrolidone group, e.g. polyvinylpyrrolidone. If PVP is used it may have a K-value of K-10.

In accordance with another feature of the invention, the optional gelling agent is a gelling agent having 0.5 to 4% by volume of the system. The optional gelling agent may be a polymer of the pyrrolidone group, e.g. ACP-1040.

With the above objects in view there is also provided, in accordance with the invention, a chemical drug delivery system for the transdermal delivery of high molecular weight drug actives, comprising: a drug active encapsulated in an encapsulating polymer with a skin penetrant enhancer. The drug active is encapsulated in microspheres being between 0.001 μm and 50 μm in size, preferably not more than 0.9 μm. The encapsulating polymer may be an alginate, e.g. sodium alginate. The crosslinker may be a chitin. The skin penetrant enhancer may be a pyrrolidone, e.g. PVP.

The patch assemblies consist of a base in which the steady state dosage is contained and individual "tear and release" or "pull and release" reservoirs. The reservoirs contain medicament which can be the same as contained in the base or various unit dosages of the base or entirely different synergistic medicaments.

Further objects and ancillary benefits will be apparent from the disclosure of the invention which consists of a multiple unit-dose transdermal patch assembly. This invention, in combination with several inventions disclosed and claimed in our copending applications which are herein incorporated by reference, includes the various drugs that can be delivered in unit doses, configurations of such assemblies, storage of the drugs within the assembly, and delivery systems for the drugs from storage areas in the assembly to the skin, various systems for activating each unit-dose of the assembly, various means for indication activation of each unit-dose, and skin enhancers.

The assembly of this invention comprises a drug-impervious support having impressed therein a series of compartments, each compartment being a reservoir for a unit-dose of the drug actives to be transdermally administered, adhesive means for adhering said support with the open face of the reservoir containing the drug actives being juxtaposed to the skin. Individual resealable closure means are provided containing the drug actives within the reservoir.

The resealable closure means on each unit dose reservoir are preferably provided with indicia for indicating that the unit dose has been released for administration. Among such indicia useful for indication of actuation and initiation of release of the unit dose, are colored stains or olfactory substances such as perfumes released upon actuation of the unit dose seal.

The drug-impervious support, impressible to form reservoirs for the drug actives and associated vehicles may be formed from flexible or rigid materials. Useful impervious materi-als include fabrics impregnated with film rendering the fabrics impervious to the drugs and vehicles, regenerated cellulose (cellophane), ABS polymer/cellulose acetate, ethyl cellulose, copolymers of plasticized vinylacetatevinylchloride, polyethylene terephthlate; polyethylene, polypropylene, nylon film or nylon fabric impregnated with drug impervious films, polyvinylidene chloride, impregnated and coated papers and metallic foils, metalized shaped films of PVC, ABS and other shapeable polymeric sheets or films. The unit dose reservoirs of the assembly may be impressed or molded into the polymeric and impregnated materials or they may be formed by sealing the peripheries of impervious material layers to form pouches which, upon loading through openings, will become drug reservoirs. Useful dimensions for such reservoirs are approximately one inch by two inches and up to about one quarter to half inch in thickness. The size of each reservoir is deter-mined by the volume of the unit dose to be administered. The volumes exemplified are sufficient for most unit doses for transdermal delivery of the drugs, but larger or smaller volumes may be used. The drugs and their adjurants are dissolved, suspended, absorbed or contained in matrices or solutions. Useful matrices are gels of bipolymers i.e. alginates, gelatins, chitin, PVP, etc.

While the examples above disclose rectangular reservoirs, as they permit adjacent positioning of individual unit doses in a multiple dose assembly, the reservoirs in pouch or container form may also be circular, oval or irregular in form depending on positioning of the assembly on the body or limbs. Configuration of the assembly is dictated by the ultimate positioning of the assembly in areas where adhesion, absorption, and contact with clothes, limbs and body hair are to be taken into account.

The number of unit doses included in each assembly depends on the size of the reservoirs to configure a convenient size. Generally, four to ten unit doses are convenient with seven units preferred as permitting a single application of the drug once a week, or several times a day depending on the medicament and clinical application.

The principle of single unit doses in the multiple dose assembly is particularly useful as only a limited amount of the drug actives is exposed to the skin for transdermal absorption. When non-segregated multiple doses, as taught by the prior art are used, there arise problems.

A variant reservoir, which is a novel aspect of this invention consists of the micro encapsulation of the drug actives in a biopolymer to protect the drug from ambient degradation as well as to serve as a reservoir for the dosage volume. Insulin is an example of such a drug active. A specific advantage for the encapsulation of the drug in such a polymer is that it allows for the controlled rate of release of the medicament by adjustment of the crosslinking, density and specific type of polymer selected for the encapsulation.

In addition, passage of the relatively large molecule of the relatively large molecule of the exemplified insulin as well as other hormone enzymes and proteins through the skin has been found to require some method of penetration enhancement. Several chemicals alone or in combination with certain solvents have been noted to promote transdermal penetration. It has been suggested that some of these materials perform their penetration by enlarging the intersticial spaces between the cells of the dermis. Such penetration vehicles or enhancers are known to the art and many are mentioned in the "Transdermal Delivery of Drugs".

Suitable penetration enhancers (flux enhancers are preferably monovalent, saturated or unsaturated aliphatic, cycloaliphatic or aromatic alcohols having from 4 to 12 carbon atoms. e.g. n-hexanol or cyclohexanol, aliphatic, cycloaliphatic or aromatic hydrocarbons having from 5 to 12 carbon atoms, e.g. hexane, cyclohexane, isopropylbenzene and the like, cyclo-aliphatic or aromatic aldehydes and ketones having from 4 to 10 carbon atoms, such as cyclohexanone, acetamide, N,N-di-lower alkylacetamides such as N, N-dimethylacetamide or N,N-diethyl-acetamide, C10–C20-alkanoylamides, e.g. N,N-dimethyllauroylamide, 1-n-C10–C20-alkylazcycloheptan-2-one, e.g. 1-n-dodeclyazacyclohephtan-2-one(Azone® laurocapram), or N-2-hydroxyethylacetamide, and known vehicles and/or penetration enhancers such as aliphatic, cycloaliphatic and aromatic esters N,N-di-lower alkylsulphoxides, unsaturated oils, halogenated or nitrated aliphatic or cyclo-aliphatic hydrocarbons, salicylates, polyalkylene glycol silicates, and mixtures thereof.

EXAMPLES

The preferred penetration enhancer for use with either micro-encapsulated or non-encapsulated calcitonin is a polymer, specifically vinylpyrollidone or polyvinyl-pyrrolidone (PVP). The drug active calcitonin of at least 15% by weight of the system is solubilized in buffered saline solution and the PVP is added at between 7 and 35% by weight of the drug active weight. A gelling agent may be admixed, preferably in the range between 1 and 3% of total volume.

The preferred penetration enhancer for use with micro-encapsulated insulin is the aforementioned "Azone®" laurocapram or 1-n-dodecylazacycloheptan-2-one because, in addition to being compatible to concentrated insulin, it is a lipophylic material.

The microencapsulation of insulin is done at low temperature i.e. below about 40° C. The insulin is solubilized at the desired concentration in a normal buffered saline (0.9N NaCl) solution of sodium alginate. The final solution contains 95% insulin. The mixture is slowly stirred to ensure uniformity and the microspheres are formed by the conventional ultrasonic spraying into a conventional suitable crosslinker. While other methods may be utilized, the ultrasonic dispersant method produces a very uniform and controlled sphere size in a short time. Micro-encapsulating cross-linkers for sodium alginate may be polycations or polyanions. A Chitosan solution, as cross linker, will produce uniform hard shell porous microspheres of 150 microns or less depending on ultrasound frequency during spraying. Other methods of drop formation may be employed as known in the art such as by gravity, drop tube or air sprays. The size of the microspheres is less than 150 microns with various ranges 1 to 150 microns being used depending on desired concentrations of the drugs to be administered.

The techniques of micro-encapsulation have been disclosed in U.S. Patents.

| | | |
|---|---|---|
| 3,161,602 | 3,270,100 | 3,341,466 |
| 3,396,117 | 3,405,070 | 3,567,650 |
| 3,875,074 | 4,145,184 | 4,277,364 |
| 4,391,909 | | |

They are incorporated herein by references.

The microspheres after washing in saline and dewatering may be re-encapsulated to reinforce their strength by use of known hard shell systems using gelatin, methylmethacrylate, chitin etc. as used in the microencapsulating of inks and perfumes. However, before the re-encapsulation, the invention includes the engrafting to the microsphere-forming biopolymer, the penetration enhancer moiety, particularly Azone®. The microspheres are coupled to the Azone® by combining a polymer matrix of PVP and glycerine with the Azone® to a 1–10% polymer matrix and then reacting therewith by contact, the microspheres under temperatures slightly above room temperatures. The "so-grafted" polymer matrix capsules are then overlaid to reinforce them or may be directly utilized by introduction into the reservoir.

Other dermal penetration of absorption enhancers may be added to a gel matrix in which the engrafted microspheres are incorporated.

It is preferably a hydrogel through which the insulin can rapidly diffuse. The absorption enhancers include surface tension modifiers for the gel matrix as well as detergents for preparing the epidermis. Also useful for inclusion are typical vasodilators including the pharmaceutically acceptable vasodilator, physalemin.

The hydrogel matrix containing the microencapsulated insulin is introduced into commercially available transdermal single patch applicators or into the aforementioned multi-dose transdermal patch assembly for unit dose application.

In animal tests patches containing insulin micro-encapsulated as above, have been applied to the shaved skin of a series of insulin animals and the microspheres have been disrupted to free the insulin into contact with the shaved skin. Within 30 minutes, all animals exhibited measurable insulin levels in the blood. By adjustment of insulin concentrations in the microspheres, therapeutic blood levels could be realized.

The commercial test patches mentioned above, are prepared using the drug impervious fabric for forming the pouch Scotchpak® Backing 1006, manufactured by 3M Corp.

The pouches were filled with the drug, hydrogel through major openings in the layer to be applied to the skin. The openings were covered with a permeable film of Cotran® 9710 (also 3M), a micro-porous polyehtylene. The patch was adhered to the shaved skin by the 3M Cotran® 9872 acrylate adhesives approved for contact with the skin and commercially offered for transdermal patch adhesive. Other useful adhesives for adhering the patches to the skin are disclosed in U.S. Pat. No. 3,797,494.

In addition to the administration of insulin by transdermal application in the form of microspheres, it is also useful to administer, transdermally, either from the same patch or reservoir or from an adjacent reservoir or compartment in the multiple assembly of this invention, an effective amount of amino-guanidine to inhibit diabetic retinopathy. This form of retinopathy is a serious complication of diabetes and is not completely countered by insulin alone.

This retinopathy results from advanced glycosylation end-products (AGEs) resulting from the improper metabolism caused by diabetes.

Aminoguanidine is an inhibitor of AGEs and has been shown by such inhibition, to mitigate the collagen crosslinking, caused by the AGEs, leading to the progressive ocular complications of diabetes.

The transdermal application of the aminoguanidine can be in the form of a gel-suspension of the aminoguanidine. It can also be introduced into the transdermal patches in frangible micro-capsules in the manner described herein for insulin. The micro-capsules of aminoguanidine may be transdermally administered either admixed with microspheres of insulin in the same patch or patch reservoir of the aminoguanidine and the insulin may be admixed with the insulin prior to formation of the microspheres.

It is also useful, under certain circumstances, to position the aminoguanidine matrix in a separate reservoir adjacent to the insulin-containing reservoir and either activating each reservoir separately or concurrently. The adjuvants useful for insulin are often also useful for the aminoguanidine.

Delivery systems for transdermal application are known in general. Various novel transdermal patches and electronic transdermal system are disclosed in several of our copending applications. We hereby incorporate by reference application Ser. No. 07/927,837, filed Aug. 10, 1992 (Multidose Transdermal Drug Delivery System), Ser. No. 07/952,049, filed Sep. 28, 1992 (Selectable Dosage Transdermal Delivery System) and Ser. No. 08/003,095, filed Jan. 11, 1993 (Electronic Transdermal Delivery System).

In general, all of our novel systems as well as various mechanical systems of the prior art are useful for the transdermal delivery of high molecular weight drugs in combination with the polymer enhancer. Particularly good results have been achieved in experiments with insulin and calcitonin together with vinylpyrrolidone (PVP), but other hormones and drugs having a molecular weight of between 500 and 25,000 daltons are within the scope of this invention. Also, the invention is applicable to both encapsulated and non-encapsulated drug actives.

DESCRIPTION OF THE PREFERRED EMBODIMENTS

Figure 1:
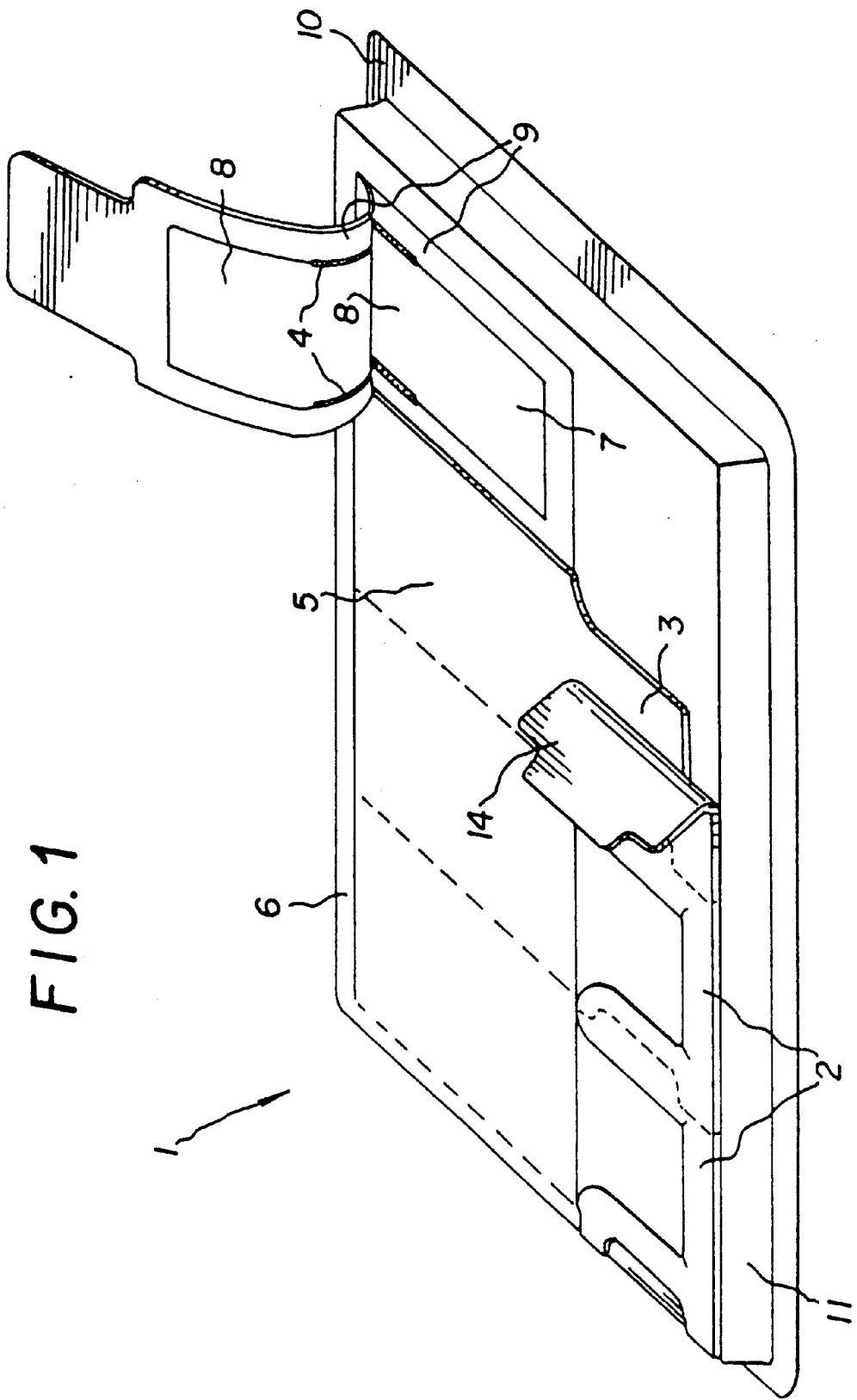
FIG. 1 is a perspective view of a multiple unit dose patch assembly.
Figure 2:
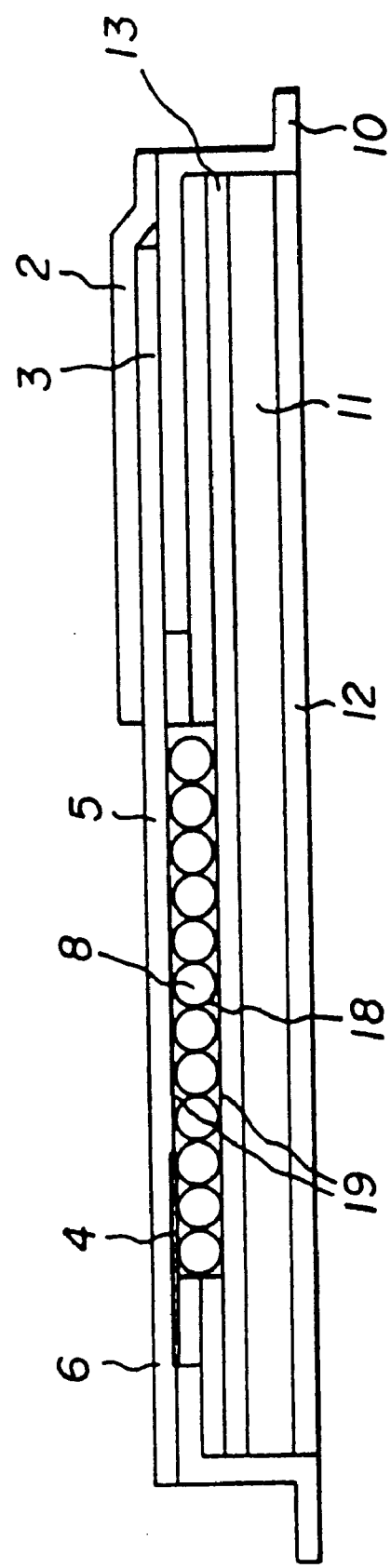
FIG. 2 is a cross-sectional view through the assembly of FIG. 1.

Referring now to the figures of the drawing in detail and first, particularly, to FIGS. 1 and 2 thereof, there is seen a multidose transdermal tear-and-release patch assembly 1, comprising a laminate composite of layers forming individual unit cells 7 with each cell containing a layer of micro-encapsulated medicament 8. The assembly is a plurality of individual unit dose cells 7 having impervious walls separating each cell 7, from its respectively adjacent cell. The unit cells 7 are filled with the desired medicament (drug actives) in microcapsule form 8. The unit cells 7 may also contain a gel-like matrix 18. The layer of microencapsulated medicament 8 is adhered to the bottom of a tear strip 5 and to the top of permeable membrane 13 by microcapsule adhesive 19.

The microencapsulated medicament 8 of each unit cell 7 may be identical or may be varied. The variation of the encapsulated medicament 8 may consist of differing strengths of the medicament which may be freed to the skin in response to variations in the clinical condition. It is also possible to provide in adjacent cells 7, differing medicaments, for example insulin in one and aminoguanidine in the other. These medicaments are related to the individual condition for which the patch is prescribed and thus, such a combination therapy is advantageous.

The unit dose cells 7 are closed to include the unit dose of encapsulated medicament 8 and gel matrix 18 by the overlaid tear strip 5 and the underlying permeable membrane 13. If necessary, the permeable membrane 13 may be utilized to control the rate of passage of encapsulated medicament 8 from the unit cell 7 into the transfer gel 11 after activation of the unit dose.

Each unit dose is activated by a two-step process. Step #1 is the removal of a security strip segment 2 by pulling back on a tab 14, which thereby exposes a tear-and-release tab 3. The purpose of the security strip 2 is to prevent any accidental release of the medicament. In step #2, each unit dose is individually activated by pulling up the tear and release tab 3 located on the end of each tear strip 5. When the tear strip 5 is pulled back to its attachment area 6, activation indicator 4 is released to provide the patient with a confirmation of the full activation of medicament 8. As the tear strip 5 is pulled back, the frangible medicament capsules are ruptured, thereby releasing the medicament 8, which diffuses through the permeable membrane 13, into the transfer gel 11 and through a patch/skin interface membrane 12 and is ready for absorption into the skin. The skin patch interface membrane 12 may be completely pervious to the contents of the cell. The transfer gel 11 may or may not contain a steady state medicament in appropriate dosage as required by the individual patient.

The tear strip 5 is secured to the unit dose 7 by an attachment area 6 where it is hinged at that point. In addition, it is adhered to the periphery of the unit dose 7 by a reservoir perimeter adhesive 9, which serves as the seal for unit dose 7. The tear strip 5 is provided with sufficient peripheral surface for reclosure of unit dose 7 by repositioning the tear strip 5 on the assembly 1 via reservoir perimeter adhesive 9.

The entire assembly is fastened to the skin by an adhesive border 10 which is adhesive coated to ensure positioning on the skin. The adhesive border 10 is preferably formulated to allow for repositioning of the assembly.

Figure 3:
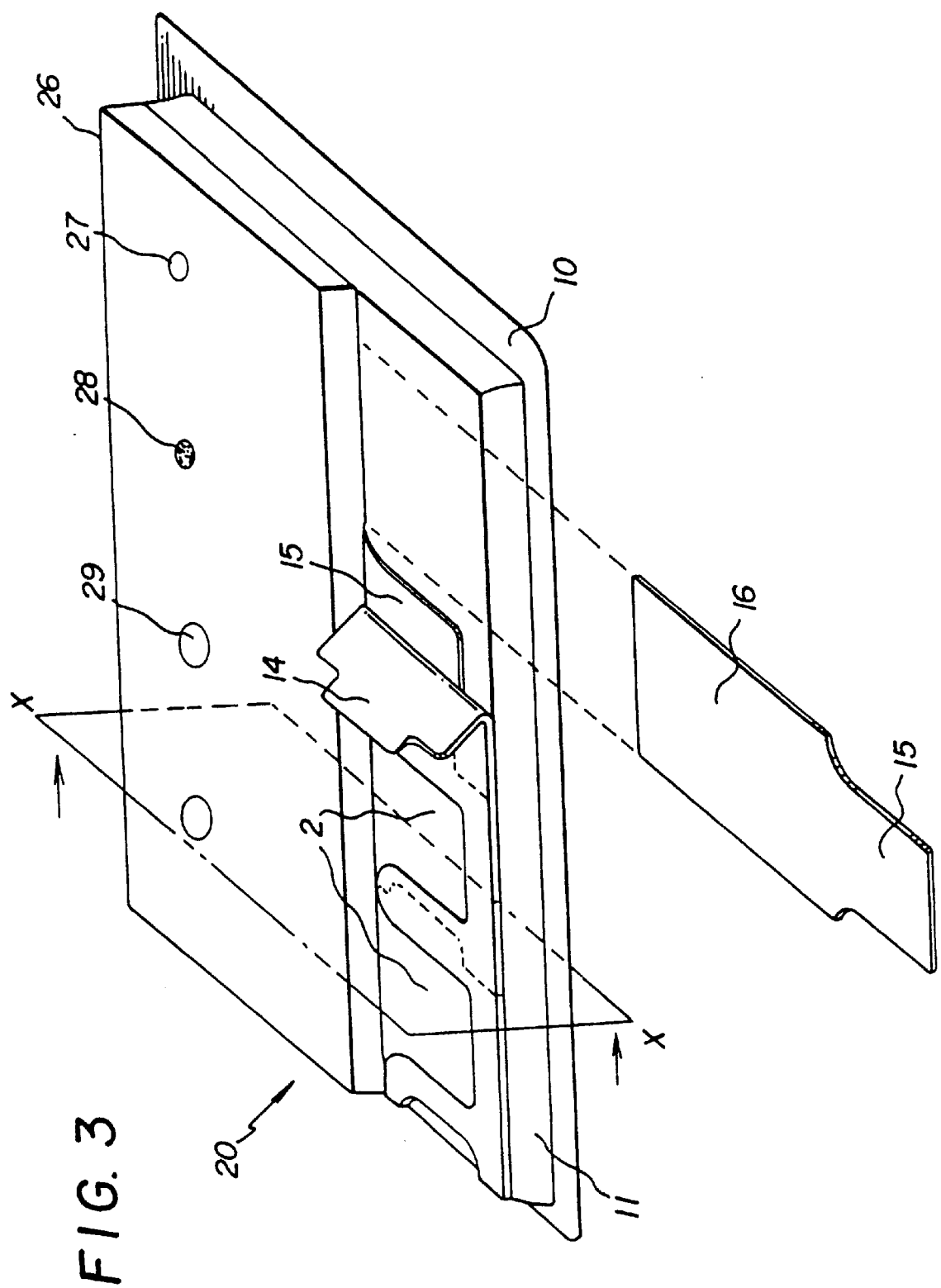
FIG. 3 is a perspective view of another embodiment of the transdermal patch assembly with filling ports and filling septa.
Figure 4:
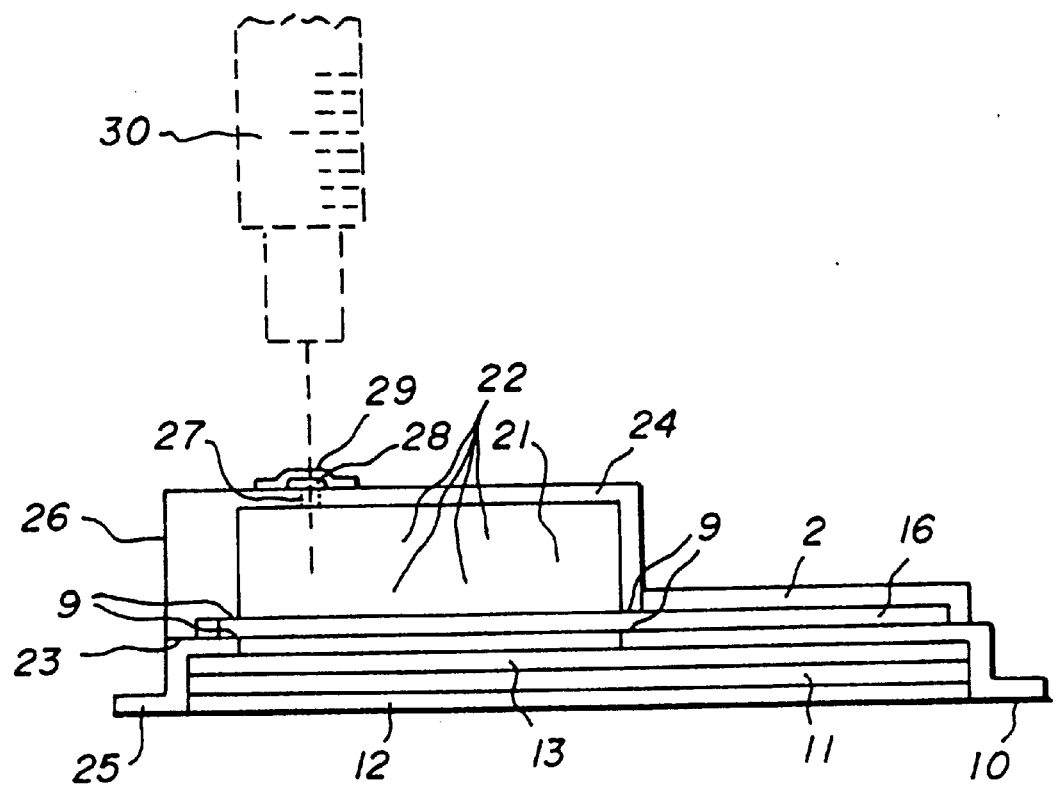
FIG. 4 is a cross-sectional view of the assembly of FIG. 3 along the plane X—X as seen in the direction of the arrows, additionally indicating a syringe for filling the medicament pouch through a fill port.
Figure 6:
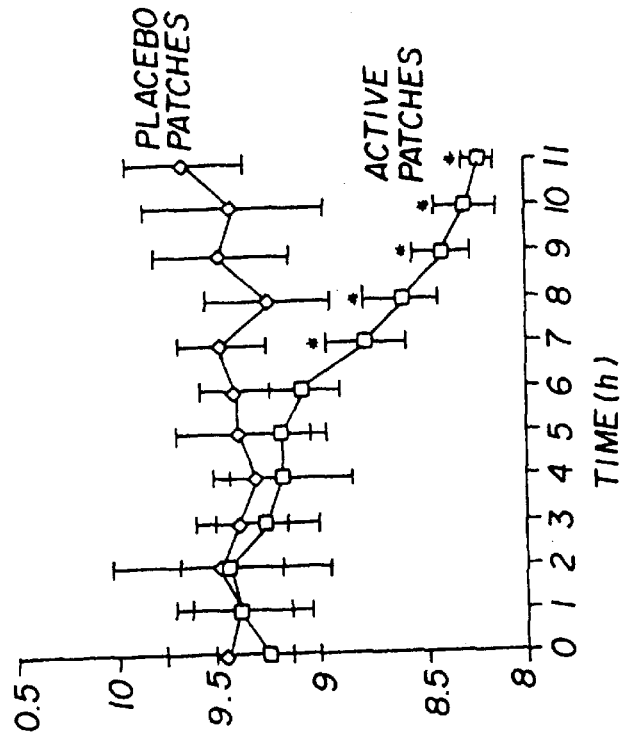
FIGS. 5–13 are clinical test result diagrams showing serium calcium levels and calcitonin levels.
Figure 5:
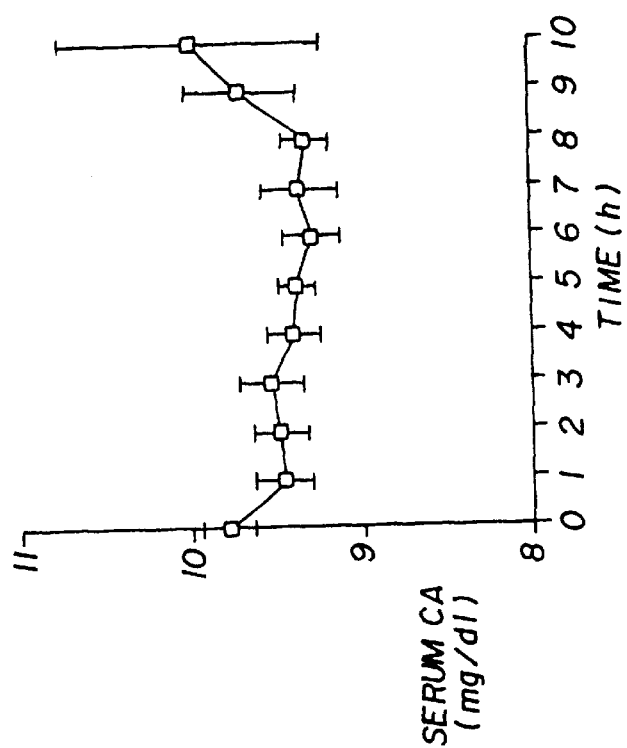
Figure 8:
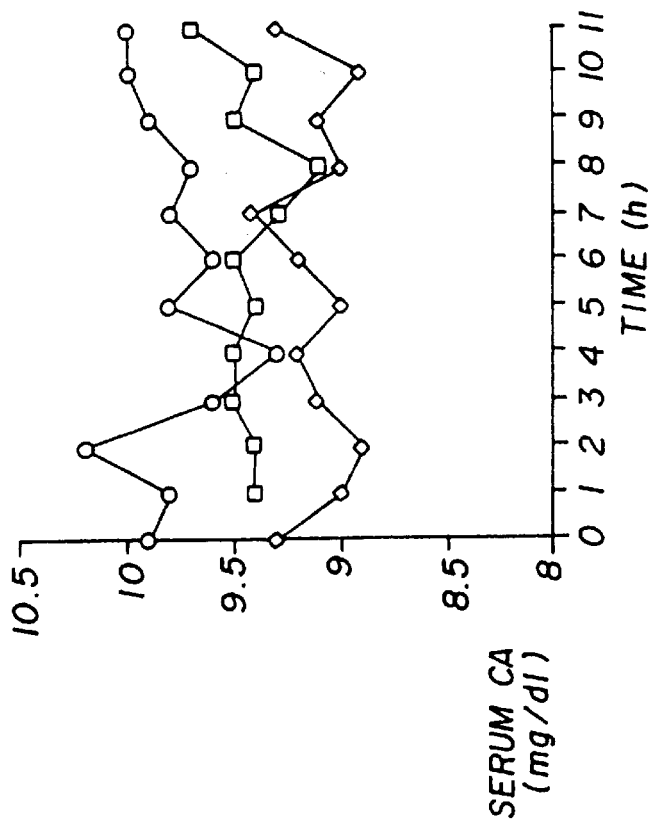
Figure 7:
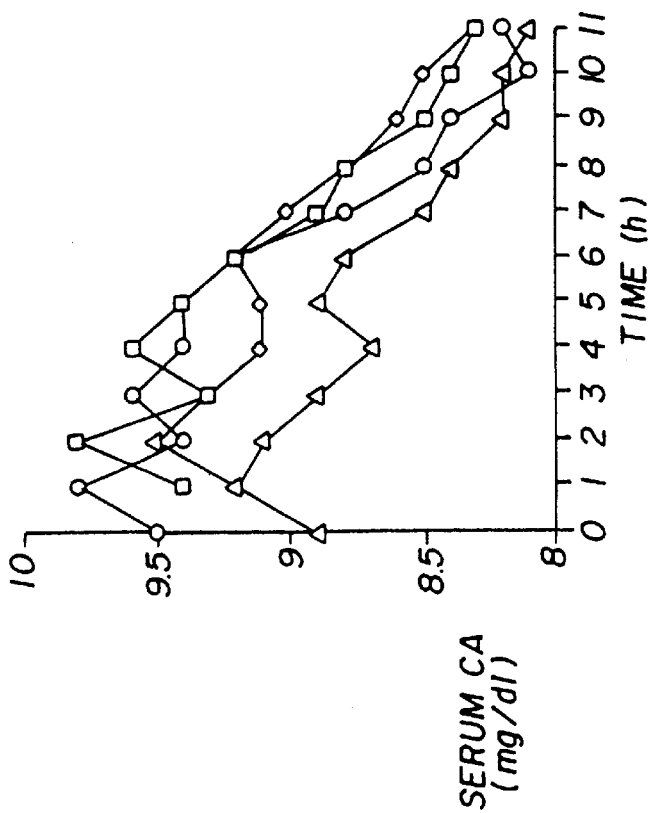
Figure 10:
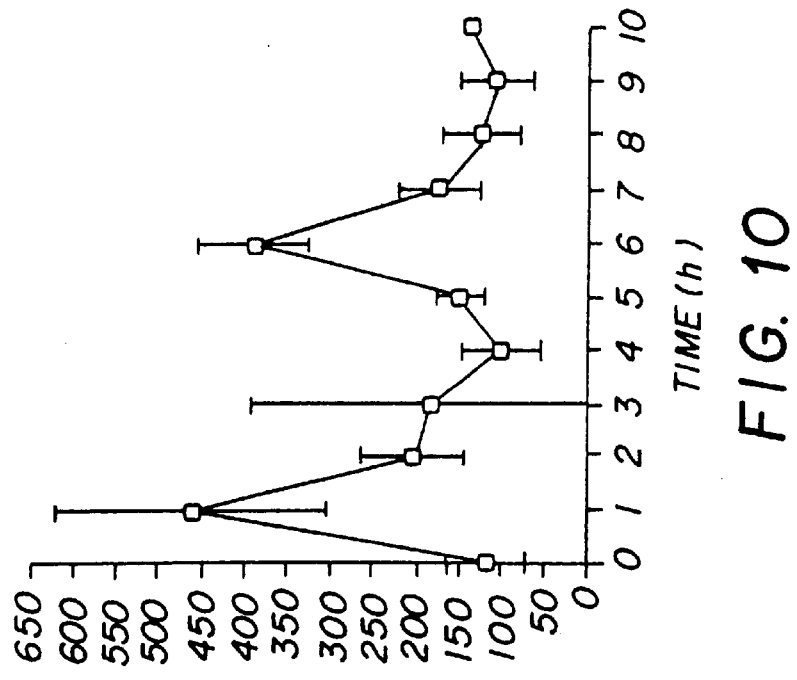
Figure 9:
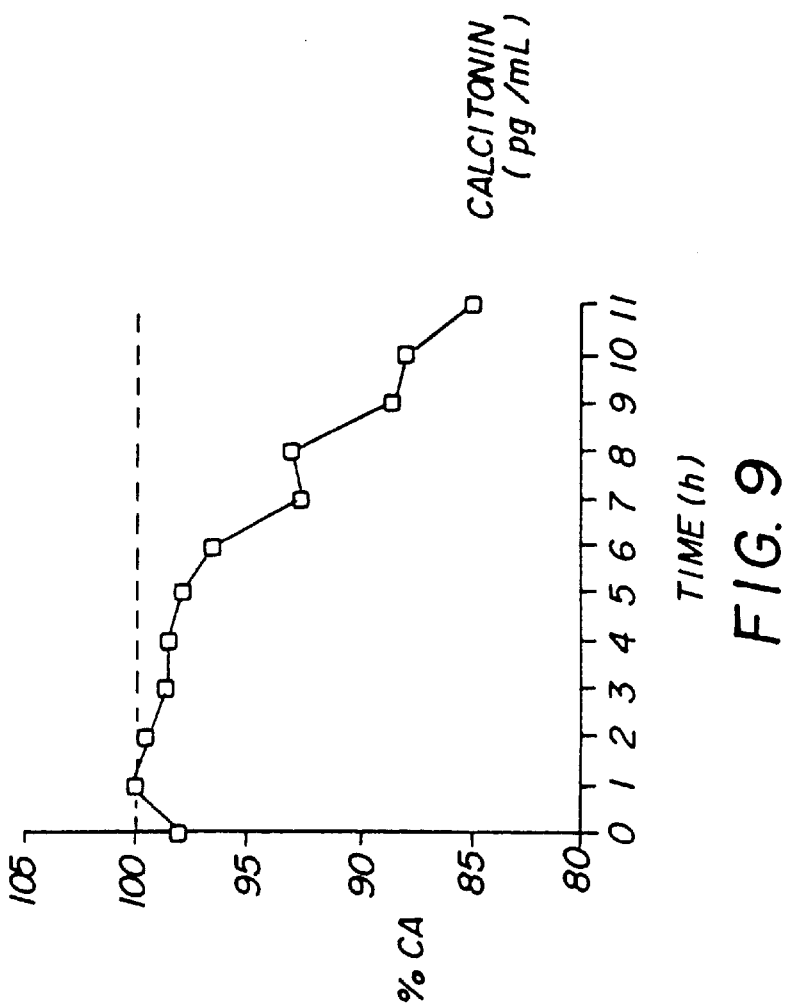
Figure 12:
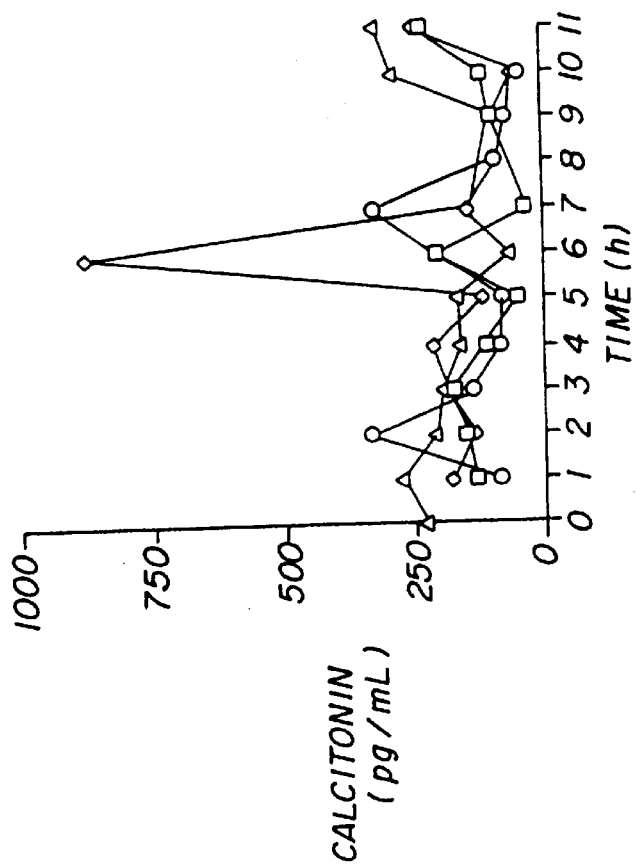
Figure 11:
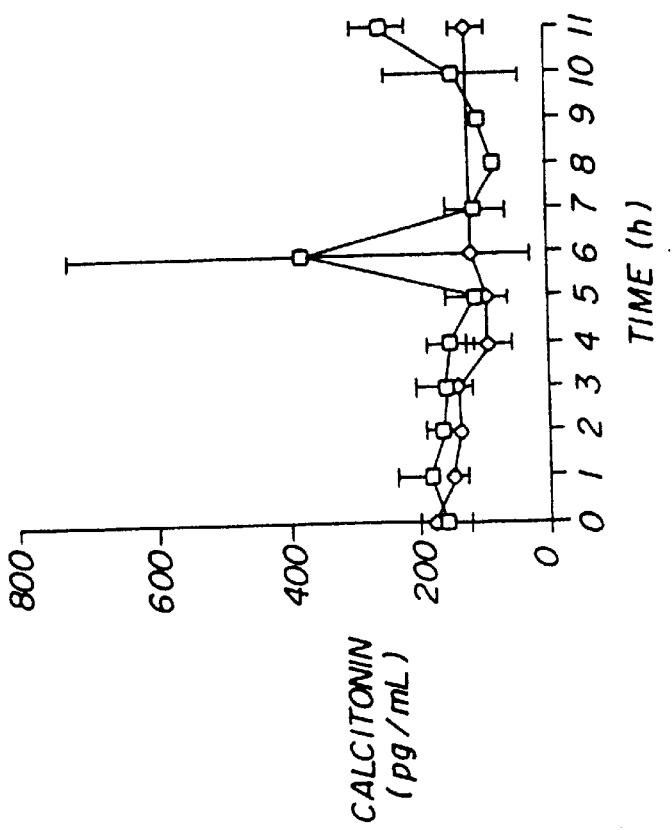
Figure 13:
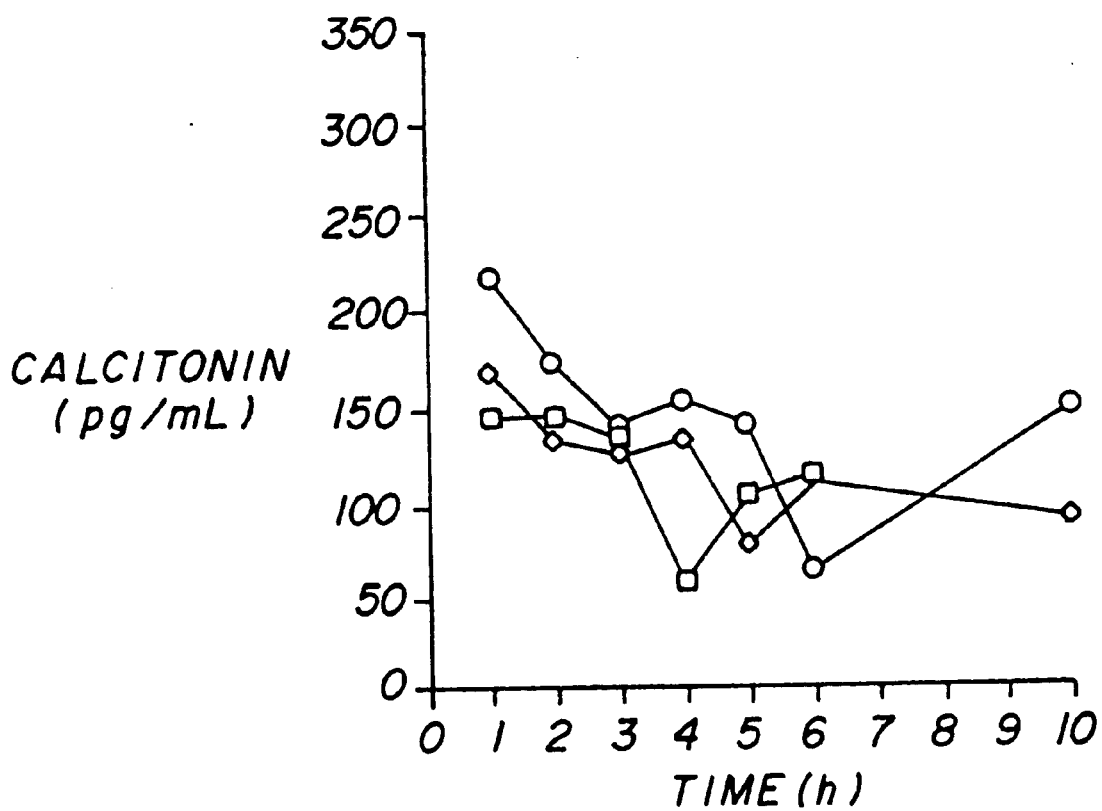

Referring to FIGS. 3 and 4, which show a multi-unit dose transdermal pull pouch assembly 20, comprising a laminate composite of layers forming individual medicament drug wells 21 containing medicament 22 in a plurality of forms, including but not limited to liquid, gel, microencapsulation or gas. The assembly 20 defines a series or plurality of individual dose medicament wells 21 having impervious walls separating each medicament well from its adjacent well. The medicament within each well 21 may be identical or may be varied, as mentioned in the context of the embodiment of FIGS. 7 and 8. The pull pouch medicament 22 is closed within the medicament well 21 by an overlaid drug impervious support 24 and an underlying impervious pull pouch strip 16.

Each unit dose of medicament is activated by a two-step process, similar to that explained in the context of FIGS. 1 and 2. Step #1 is the removal of the security strip segment 2 by pulling back on its tab 14, which thereby exposes pull pouch tab 15. The purpose of the security strip is to prevent any accidental release of the medicament. In step #2 each unit dose is individually activated by pulling on pull pouch tab 15 until pull pouch strip 16 is removed from the assembly 20. Removal of the impervious pull pouch strip 16 allows the pull pouch medicament 22 to diffuse through the permeable membrane 13, into the transfer gel 11 and through the patch/skin interface membrane 12 and is ready for absorption into the skin.

The pull pouch strip 16 is secured to assembly 20 at its posterior end 26 by adhesive 23. The posterior end 26 of the pull pouch strip 16 is perforated and will tear free from the pull pouch assembly 20 upon pulling on the pull pouch tab 15.

A basal attachment membrane 25 is disposed below the pull pouch strip 16, which membrane 25 has on its upper surface reservoir perimeter an adhesive 9. The adhesive extends from the perimeter of the medicament well 21 to the perimeter of the pull pouch strip 16. Above the pull pouch strip 16 is a drug impervious support 24 which has on its lower surface the reservoir perimeter adhesive 9, which adhesive extends from the perimeter of the medicament well 21 to the perimeter of the pull pouch strip 16. Above the pull pouch strip 16 is a drug-impervious support 24 which has on its lower surface the reservoir perimeter adhesive 9, which adhesive extends from the perimeter of medicament well 21 to the perimeter of the pull pouch strip 16. The upper and lower surfaces of the pull pouch strip 16, which come into contact with the reservoir perimeter adhesive 9 are made from a non-adhering material, thereby permitting the pull pouch strip 16 to be removed from the assembly 20 without affecting the adhesive which is above and below it.

The pull pouch strip 16 is manufactured from a non-adhesive material. Upon removal of the pull pouch 16 from the assembly 20, the reservoir perimeter adhesive 9 on the surfaces of the basal attachment or occulatory membrane 25 and the drug impervious support 24 adhere to one another forming a complete seal and preventing any leakage of the medicament 22.

The basal attachment membrane 25 extends past the patch/skin interface membrane 12 providing a surface to attach the assembly 20 to the skin via the border adhesive to ensure positioning on the skin. The adhesive is preferably formulated to allow for repositioning of the assembly.

If the medicament well 21 contains medicament in the microencapsulated form, pulling the pull pouch strip 16 from the assembly will rupture the microcapsules, thereby releasing the medicament for diffusion to the skin.

The pull pouch strip 16 may include indicators to show the release of medicament from the medicament well 21. Such indicators would alert the patient as to the activation state of the medicament within the individual dose unit of the assembly 20. Indicators may consist of pigments released from microcapsules as known in the art, olfactory signals similarly microencapsulated and released by removal of pull pouch strip 16 or visual indicators located on the pull pouch strip 16.

In an additional embodiment, the uppermost composite layer of the pull pouch assembly 20 has a fill port hole 27, above each medicament well 21, into which is placed or fitted a filling septum which allows for the aseptic introduction or withdrawal of medicament into or from the medicament well 21. The preferred method for the introduction or withdrawal of medicament is by syringe and needle. The filling septum 28 provides both a method for the medicament to be introduced into the medicament well 21 and also self-seals and protects the medicament after it has been inserted. Individually covering each fill port 27 and filling septum 28 is a septum protector 29, which is to be removed prior to insertion of medicament. The medicament well 21 may or may not contain gel or other non-medicament or medicament components as required.

This assembly is advantageous as it allows for customizing of the medicament to meet specific clinical needs which will be obvious to those skilled in the healing arts.

Clinical Tests

As the literature is void of any teaching regarding the successful transdermal administration of drugs with high molecular weight (i.e. above 50 daltons and particularly in the 4000–6000 range of insulin and calcitonin), we show herein the results of a two-day human test.

The "Calcitonin Test" demonstrated the viability of transdermal delivery of calcitonin to humans via the above-described mechanical patch delivery system. The established test parameters were found in the measurement of serum calcium and calcitonin levels in test subjects. Reference control was established with a number of placebo patches concomitantly applied.

The test was conducted as a blind study, wherey two patient control subjects were given placebo patches without calcitonin and six patients were given calcitonin patches. 200 IUs of active drug was present in patches of 25 $cm^2$.

With reference to FIGS. 5–13, it is clearly seen that the transdermal delivery of calcitonin (as indirectly shown by the vastly lowered serum calcium levels and as directly shown by the increased calcitonin levels) was extremely successful. Most importantly, the delivery was at clearly therapeutic levels.

Figure 14:
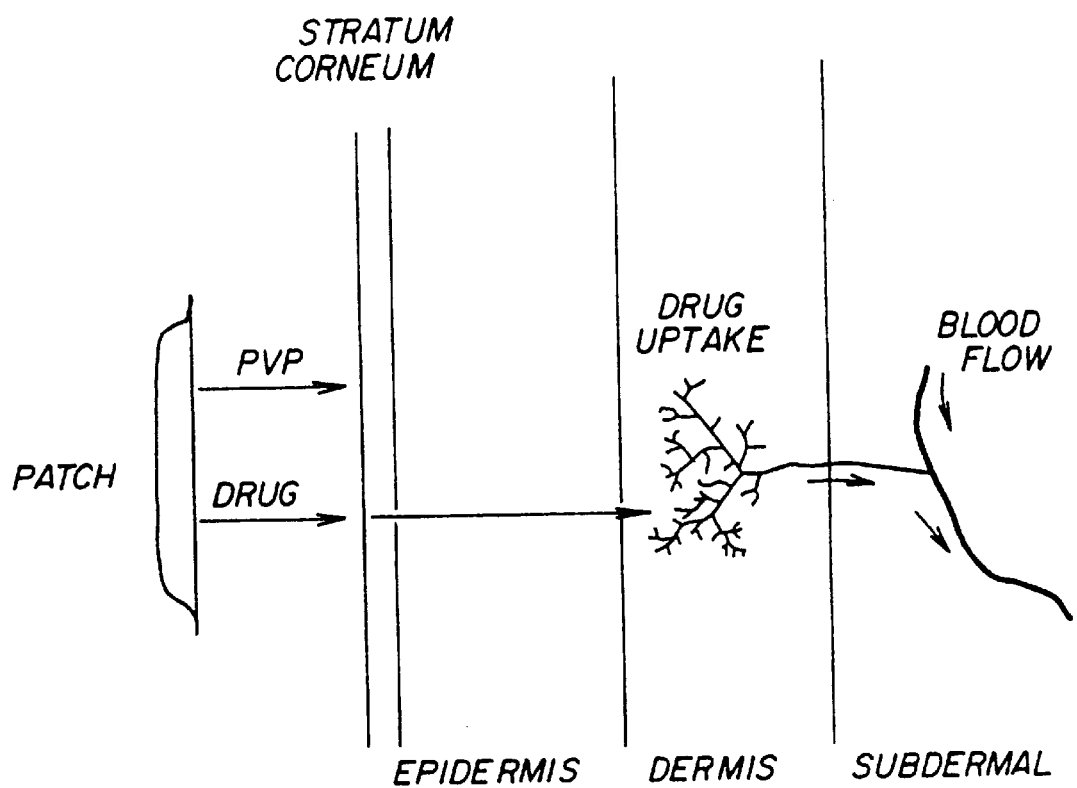
FIG. 14 is a diagrammatic illustration of transdermal drug administration.

Referring now to FIG. 14 (adapted from "Transdermal Drug Delivery System with Enhanced Skin Permeability", Chien and Lee, American Chemical Society, ACS Symposium Series; 1987; page 286), it is seen that skin permeation may be enhanced by first releasing a skin enhancer so as to modify the skin permeability. This is followed by the release of the drug active at therapeutic levels. Comparative tests between the use and non-use of enhancers are reported in the literature.

In closing it is noted that the application of this invention, i.e. the transdermal delivery of high molecular weight drugs is not limited to the patch assemblies or the electronic delivery system described above and in our copending applications. Topical creme application is equally possible, and/or the application by the known "wet bandaid" technique. Suitable gelling agents are well known in the art.

Preliminary studies have shown very promising results in terms of drugs with a molecular weight at a lower boundary of what is usually defined as a high molecular weight drug. For instance, transdermal delivery is possible for

| Vasotec | 384 |
|---|---|
| Inderal | 295 |
| Nifedipine | 346 |
| Ibuprofen | 206 |
| Theophylline | 180 |
| Mercaptopurine | 152 |
| Flurouracil | 130 |
| Urea | 60 |
| Propylthioruacil | 170 |
| Lidocane | 234 |
| Allopurinol | 136 | where the numbers indicate the molecular weights.

The present invention is directed to the discovery that polyvinylpyrrolidone acts as a highly effective skin enhancer to effect the transdermal delivery of high molecular weight drugs having a molecular weight above 50 daltons to a patient and thereby effect the achievement of therapeutic levels of such drugs in the systemic distribution system. Among such high molecular weight drugs successfully administered with the assistance of polyvinylpyrrolidone according to this invention are calcitonin (molecular weight approximately 6000 daltons) and insulin (molecular weight approximately 4000 daltons). It is a measure of the unexpectedly great effectiveness of polyvinylpyrrolidone as a skin enhancer according to this invention that only modest use levels are needed, namely 7% to 35% of the weight of the drug active in the composition. Thus the composition of this invention contains considerably more drug active than polyvinylpyrrolidone skin enhancer, i.e. 100 parts by weight of drug active to 35 parts by weight or less (all the way down to a mere 7 parts by weight) of polyvinylpyrrolidone. A further consequence of the unexpectedly great effectiveness of polyvinylpyrrolidone and modest use levels thereof in the composition of this invention is that high concentrations of drug active are accommodated, namely at least 15% by weight of the composition.

We claim:

1. A system for effecting delivery of high molecular weight drug actives by transdermal administration, consisting essentially of at least 15% by weight of a drug active having a molecular weight ranging from 50 daltons to 25000 dalton, a polymer which is polyvinylpyrrolidone, a weight of said polymer being 7 to 35% by weight of said drug active, and an optional gelling agent having from 0 to 20% by volume of the system.

2. The polymer system according to claim 1, wherein said drug active is Calcitonin.

3. The polymer system according to claim 1, wherein said optional gelling agent is a gelling agent having 0.5 to 4% by volume of the system.

4. The system according to claim 1, wherein said optional gelling agent is a polymer having a pyrrolidone group.

5. A method of transdermally administering a high molecular weight drug, which comprises: mixing a polymer skin enhancer which is polyvinylpyrrolidone, and a drug active having a molecular weight above 50 daltons and up to 25000 daltons in a ratio such that the drug active is at least 15% of the mixture and polyvinylpyrrolidone is 7 to 35% by weight of the drug active, and applying the said mixture of polyvinylpyrrolidone and the drug active to skin of a patient thereby effecting transdermal absorption of the drug by the patient without requiring the use of an electrically powered iontophoretic agent delivery device.

6. The method according to claim 5, which comprises adding a gelling agent of up to 20% of volume to the polymer skin enhancer and the drug active prior to applying to the skin of the patient.

7. A composition for effecting delivery of high molecular weight drug actives by transdermal administration, consisting essentially of at least 15% by weight of a drug active having a molecular weight of more than 50 daltons and up to 25000 daltons, a biocompatible polyvinylpyrrolidone in an amount of 7 to 35% by weight of said drug active, a solubilizing amount of a buffered saline solution, and an optional gelling agent having from 0 to 20% by volume of the composition.

8. The composition according to claim 7, in which the drug active has a molecular weight of more than 500 daltons.

9. The composition according to claim 7, in which the optional gelling agent has from 0.5 to 4% by volume of the composition.

10. The composition according to claim 7, in which the drug active is calcitonin.

11. The composition according to claim 7, in which the drug active is insulin.

12. A method of effecting delivery of high molecular weight drug actives by transdermal administration, comprising the application to human skin of a composition according to claim 7.

13. A system for effecting delivery of high molecular weight drug actives by transdermal administration, consisting essentially of at least 15% by weight of a drug active having a molecular weight ranging from 50 daltons to 25000 daltons, a polymer which is polyvinylpyrrolidone, a weight of said polymer being 7 to 35% by weight of said drug active, and an optional gelling agent having from 0 to 20% by volume of the system, and further including a patch assembly.

14. A system for effecting delivery of high molecular weight drug actives by transdermal administration, consisting essentially of at least 15% by weight of a drug active having a molecular weight ranging from 50 daltons to 25000 daltons, a polymer which is polyvinylpyrrolidone, a weight of said polymer being 7 to 35% by weight of said drug active, and an optional gelling agent having from 0 to 20% by volume of the system, and further including electronic delivery of said drug active.

15. A system for effecting delivery of high molecular weight drug actives by transdermal administration, consisting essentially of at least 15% by weight of a drug active having a molecular weight ranging from 50 daltons to 25000 daltons, a polymer which is polyvinylpyrrolidone, a weight of said polymer being 7 to 35% by weight of said drug active, and an optional gelling agent having from 0 to 20% by volume of the system in which said drug active is encapsulated in microspheres.

16. A system for effecting delivery of high molecular weight drug actives by transdermal administration, consisting essentially of at least 15% by weight of a drug active having a molecular weight ranging from 50 daltons to 25000 daltons, a polymer which is polyvinylpyrrolidone, a weight of said polymer being 7 to 35% by weight of said drug active, and an optional gelling agent having from 0 to 20% by volume of the system, and a penetration enhancing amount of an additional enhancer selected from the group consisting of acetamide, N,N-dimethylacetamide, N,N-diethylacetamide, $C_{10}$–$C_{20}$alkanoylamides, 1-N-$C_{10}$–$C_{20}$-alkylazacycloheptan-2-one, N-2-hydroxyethylacetamide, dimethyl sulfoxide, salicylates, polyalkylene glycol silicates, and mixtures thereof.

17. A system according to claim 16 in which the additional enhancer is acetamide.

18. A system according to claim 16 in which the additional enhancer is N,N-dimethylacetamide.

19. A system according to claim 16 in which the additional enhancer is N,N-diethylacetamide.

20. A system according to claim 16 in which the additional enhancer is N,N-dimethyllauroylamide.

21. A system according to claim 16 in which the additional enhancer is 1-Ndodecylazacycloheptan-2-one.

22. A system according to claim 16 in which the additional enhancer is a dimethyl sulphoxide.

23. A system according to claim 16 in which the additional enhancer is a salicylate.

24. A system according to claim 16 in which the additional enhancer is a polyalkylene glycol silicate.

* * * * *